US006569653B1

(12) United States Patent
Alard et al.

(10) Patent No.: US 6,569,653 B1
(45) Date of Patent: May 27, 2003

(54) METHOD FOR PRODUCING ETHANOL WITH FREQUENT INPUT OF YEAST

(75) Inventors: Georges Maurice Alard, Guise (FR); Philippe Jean Roux, Saint-Quentin (FR); Alain Yves Gérard Mourin, Ribemont (FR); Luc Robert Brasseur, Pleine-Selve (FR)

(73) Assignee: Bio-Ethanol Nord Picardie, Origny-Sainte-Benoite (FR)

( * ) Notice: Subject to any disclaimer, the term of this patent is extended or adjusted under 35 U.S.C. 154(b) by 0 days.

(21) Appl. No.: 09/890,547

(22) PCT Filed: Jan. 28, 2000

(86) PCT No.: PCT/FR00/00199
§ 371 (c)(1),
(2), (4) Date: Jan. 14, 2002

(87) PCT Pub. No.: WO00/46387
PCT Pub. Date: Aug. 10, 2000

(30) Foreign Application Priority Data

Feb. 4, 1999 (FR) .............................................. 99 01297

(51) Int. Cl.⁷ ........................... C12P 7/06; C12C 11/00; C12G 1/08

(52) U.S. Cl. ......................................... 435/161; 426/11
(58) Field of Search ............................. 435/161; 426/11

(56) References Cited

U.S. PATENT DOCUMENTS 4,419,448 A * 12/1983 Kretz ........................... 435/161
5,231,017 A * 7/1993 Lantero et al. .............. 435/161

FOREIGN PATENT DOCUMENTS

CH         554 414          9/1974

OTHER PUBLICATIONS

Delia–Dupuy et al. Microbiol. Ailments Nutr. vol. 13, 1995 pp. 349–359.*

* cited by examiner

*Primary Examiner*—Herbert J. Lilling
(74) *Attorney, Agent, or Firm*—Knobbe, Martens, Olson & Bear, LLP

(57) ABSTRACT

In this process for producing ethanol by enzymatic treatment of a must of a starchy plant material with yeasts of the genus Saccharomyces, all the old yeasts are replaced with fresh yeasts in order to keep the fermentation time between 20 and 24 hours.

14 Claims, No Drawings

METHOD FOR PRODUCING ETHANOL WITH FREQUENT INPUT OF YEAST

REFERENCE TO RELATED APPLICATIONS

This is the U.S. national phase under 35 U.S.C. §371 of International Application PCT/FR00/00199, filed Jan. 28, 2000 and claims priority under 35 U.S.C. §119(a) from French Patent Application No. 99/01297, filed Feb. 4, 1999.

FIELD OF THE INVENTION

The present invention relates to processes for producing ethanol from starchy plant raw material. The invention applies particularly to the production of ethanol as a fuel, but also to the chemical, pharmaceutical and cosmetics industries and, after rectification in order to remove aromatic substances, the food industry. The invention especially uses as starting material a wheat, corn, barley, sorghum, rye or rice must.

BACKGROUND OF THE INVENTION

A process for producing ethanol which consists in subjecting a starchy plant material must to an enzymatic liquefaction treatment in order to obtain a liquefied must is already known. The liquefied must is then subjected to an at least partial enzymatic saccharification treatment in order to obtain a saccharified must. The starch is at least partially converted into glucose. The saccharified must is then divided into a first portion and a second portion. The first portion of the saccharified must is diluted with a diluent and is placed in contact in a prefermenter with a yeast of the genus Saccharomyces in order to obtain a yeast suspension. The proportion of diluent, which is generally water and/or vinasse, is such that the alcoholic degree of the yeast suspension is less than 6% by volume, with the effect that an excessively high alcohol concentration does not prevent the yeasts from growing. This yeast suspension is then placed in contact with the second portion of the saccharified must in a fermenter for a time which is sufficient to obtain a wine with an ethanol content above a given threshold. In usual practice, this time is proportionately longer the higher the ethanol content. For example, when the saccharification time is 20 h, a contact time in the fermenter or fermentation time of 40 h must commonly be allowed for in order to obtain an ethanol content of greater than 9% with a sugar content of less than 1 g/l. It has already been recommended to reduce the time for the saccharification operation to 10 h by arranging it such that the saccharification takes place also during the fermentation time which is kept at 40 h. The total time for the operations is thus 50 h. In order to obtain ethanol, the wine is distilled. During this distillation, an extraction of the "unpleasant tastes", which correspond especially to the esters, is carried out so as to be able to obtain ethanol containing less than 500 parts of esters per million, as is commonly required for the use of ethanol as a fuel. It is also necessary to add acid to the prefermenter continuously in order to maintain a certain level of bacterial asepsis and to disinfect the circuits with disinfectant.

SUMMARY OF THE INVENTION

The invention overcomes these drawbacks by means of a process for producing ethanol which is much shorter than the prior-art processes, which directly gives by distillation an alcohol with such a small ester content that it is no longer necessary to allow for extraction of this ester content, thereby making it possible to dispense with any addition of acid to the prefermenter and to reduce the amount of disinfectant used in the manufacturing circuits, while at the same time having, all conditions being otherwise equal, wine with a higher alcoholic degree and the same low sugar content.

The subject of the invention is a process for producing ethanol which consists in placing a starchy plant raw material must in contact with a liquefaction enzyme in order to obtain a liquefied must, placing the liquefied must in contact with a saccharification enzyme in order to obtain an at least partially saccharified must, preparing in a prefermenter a suspension of yeasts of the genus Saccharomyces in a nutrient medium, placing the saccharified must in contact with an amount of the yeast suspension which is sufficient and for a time which is sufficient to convert the sugars contained in the saccharified must into ethanol, giving a wine with a sugar content of less than 3 g/l, preferably less than 2 g/l and better still less than 1 g/l for a wine alcoholic degree of at least 9.5% on a volume-for-volume basis, and distilling the wine in order to obtain ethanol, characterized in that it consists in removing substantially all the yeasts present in the prefermenter and in replacing them therein with fresh yeasts at a time interval such that the concentration of microorganisms, other than the yeast of the genus Saccharomyces, in the prefermenter remains less than a given threshold during the interval following the replacement of the yeasts.

Specifically, it has been found, unexpectedly, that the very long contact time of the yeast suspension with the saccharified must, which was necessary hitherto, is due to the fact that in a relatively short space of time the yeast of the genus Saccharomyces suffers degeneration, mutation and/or contamination with another microorganism, especially with a yeast of the genus Brettanomyces which is much less active. By replacing all the yeasts with fresh yeasts of the genus Saccharomyces before this phenomenon takes place, and in particular preferably before there are $10^7$ cells per milliliter, and better still $10^5$ cells per milliliter, of a microorganism other than the yeast of the genus Saccharomyces in the prefermenter, the activity of the fermentation yeasts is maintained, thereby making it possible to reduce the contact time in the fermenter, to have virtually no more ester during the distillation, to have a higher alcoholic degree, to dispense with the need to add acid to the prefermenter and to reduce the amount of disinfectant. The freshness of the yeast suspension is of fundamental importance regarding the duration of the step for converting the sugars into ethanol. Supplying fresh yeasts to yeasts that are already contaminated gives only a very transient improvement in the contact time required. In order to keep the continuously shortened contact time desired, it is necessary to remove virtually all the old yeasts before adding fresh yeasts.

DETAILED DESCRIPTION OF THE INVENTION

The presence of Brettanomyces in the prefermenter may be detected by taking a sample of the yeast suspension and examining it by microscope. Whereas Saccharomyces, and especially *Saccharomyces cerevisiae*, have an ovoid shape, Brettanomyces have an elongate shape. It is also possible to know by experience the interval to observe for the addition of the fresh yeasts and to systematically replace the spent yeasts with Saccharomyces yeasts at a time interval of less than 4 days.

According to one preferred embodiment, the process consists in diluting a first portion of 10 to 30% and preferably of 15 to 20% of the weight of the saccharified must in order to obtain a weak must, the rest of the saccharified must constituting a strong must, in prefermenting the weak must in the prefermenter in order to obtain a prefermented must and in placing the strong must in the presence of the prefermented must in a fermenter for a time which is sufficient to obtain wine.

Preferably, fresh yeasts are supplied to the prefermenter in an amount such that a concentration at least equal to 106 cells per milliliter approximately and preferably $10^7$ cells per milliliter is obtained in the prefermenter.

It has been found, especially for a threshold of 9.5% for the wine ethanol content, that the sum of the saccharification time and the contact-time in a fermenter is only 35 h.

The first stage of the process according to the invention consists in subjecting a starchy plant material must to an enzymatic liquefaction treatment in order to obtain a liquefied must.

The plant material, in particular wheat, is ground, for example by one or two treatments in a hammer mill (of the brand PROMILL Promill-Stolz, RN 12 Serville, 28410 BU, 3000 rpm, or of the brand JACKERING Vorsterhauser Weg 46 PO BOX 1733, 59007 HAMM) rather in the cases where the bran particles are not separated from the flour, and in one or more roll mills (in which the milling is more homogeneous) rather in the cases where the bran particles are separated from the flour, or any other type of mill. It is optionally possible, in the case of a starch refinery, to separate the flour into two grades: an A flour intended for the starch refinery process and a B flour intended for the ethanol process. The wheat may optionally be humidified to between 18 and 25% by weight before milling in order to improve the separation between the flour and the bran particles.

The flour obtained is screened. The screen retainings are recycled into the mill, such that the coarsest grains do not exceed 2.5 mm. Commonly, the percentage of particles larger than 1 mm must not exceed 10% of the total. The average mesh size of the flour is between 0.3 and 2 mm, and 0.6 constitutes a common value. The bran particles which are separated out on screening are either reintroduced into the flour or separated out. Either a wholemeal flour or a white flour is thus obtained.

In the case of a wholemeal flour, the flour is then mixed in a mixer with a solution of water, vinasse, sodium hydroxide and a liquefaction enzyme. This solution is prepared, for example, using in-line static mixers or in a preparation tank. The flour/solution mixture may be prepared either in a screw mixer (brand: PROMILL Promill-Stolz, RN 12 Serville, 28410 BU, spin speed: 700–1200 rpm) and/or then in a homogenizer (brand: APV GAULIN, pressure: about 100 bar), or in a stirred tank.

In the case of a separation of the gluten, the vinasse originating from the distillery is not recycled into the slurrying operation. The solution is prepared using starch milk originating from the starch refinery process and B flour.

A must with a solids content of 25 to 35% by weight is thus obtained. The percentage of solids is determined by the optimum solids content for functioning of the liquefaction and saccharification enzymes and out of an economic concern to have the highest possible solids content in order to limit the costs for evaporating the vinasse in the rest of the process. The amount of flour supplied to the mixer is controlled either by a metering device from SCHENCK, Chemin neuf BP 17, 78240 CHAMBOURCY, or by a weighing band.

In order to have the highest possible solids content (between 4.5 and 7% by weight) in the clarified vinasse (separation of the insoluble fraction from the vinasse by centrifugal decantation), it is sought to introduce as much vinasse as possible into the slurrying operation rather than supplying external water. This determines the fraction of vinasse relative to the water in the slurrying operation. The clarified vinasse represents from 40 to 80% by weight of the solution used to carry out the slurrying operation. The water may be a borehole water, a process liquor (evaporation condensates or aqueous distillates) or a river water which has been prefiltered through a sand filter and/or sterilized by UV radiation.

The temperature of the water/vinasse mixture is between 40° C., in order to facilitate mixing and in order to limit the energy consumption for the liquefaction, and a maximum of 70° C., so as not to gelatinize the starch during the slurrying operation. The temperature of the vinasse leaving the centrifugal decanters (GUINARD CENTRIFUGATION, ZI du Buxerioux, BP 69, 36002 Chateauroux; WESTFALIA SEPARATOR, 18, avenue de l'Europe, BP 120, 02407 Chateau-Thierry) is between 70 and 100° C. according to the distillation process (the temperature is lower in the case of a vacuum distillation). The flour is at room temperature. A plate exchanger or a tubular exchanger or any other type of heat exchanger must be provided to heat the water so as to obtain the mixture temperature mentioned above.

Depending on the liquefaction enzyme used, the pH must be adjusted with 30 or 50% sodium hydroxide or any other basifying agent. A calcium salt may optionally be used if the enzyme requires it. The enzymes used are fungal or bacterial alpha-amylases, for example Termamyl 120L type S, type L or type LS from NOVO NORDISK Bioindustries S.A., 79, av. Francois-Arago, 92017 Nanterre Cedex, France; SPEZYME AA or SPEZYME AAL from GENENCOR P.O. Box 642, Delft, Netherlands; NERVANASE or G-ZYME G995 from RHODIA, Poleacre Lane, Woodley, Stockport, Cheshire, SK6 1PQ, United Kingdom). The flow rate of sodium hydroxide is controlled by means of a pH probe installed on the water/vinasse mixture before the slurrying unit. The pH may range between 4.5 and 8 depending on the enzymes used.

The liquefaction is carried out at a temperature of between 50 and 100° C. The slurried must may be brought to this temperature either by means of a direct injection of steam into the liquefaction tank via pipes; or by means of a jet cooker, in which case the slurried must is maintained at 100–150° C. for a few seconds by means of an injection of steam into a nozzle before being rapidly cooled to between 80 and 95° C. The flow rate of enzymes may be controlled by the flow rate of flour.

The liquefaction tanks may be stirred, for example, with stirrers of the brand PMS, BP 72 91560 Crosne, with two rows of paddles for the first tank and one row for the second, spin speed: 42 rpm for the first tank, 58 rpm for the second (the spin speeds may be between 20 and 60 rpm). The residence time under these temperature conditions is between 30 minutes and two hours.

The current characteristics of the liquefaction process depending on the enzyme used are:

Temperature: 85–88° C.
pH: 5.5–6
Solids content: 32%–35%
Residence time: 1 hour
Liquefaction enzyme flow rate: about 3.5 litres/hour for a flour feed rate of 8 tonnes/hour.

The must thus liquefied is cooled in heat exchangers of conventional type (plate exchangers or tubular exchangers)

at 60° C. (temperature: dependent on the optimum working conditions of the saccharification enzymes, possibly ranging from 40° C. to 70° C.).

In certain cases, the liquefied must may be diluted with a diluent such as water or recycled vinasse originating from the distillery, as mentioned above.

The liquefied must is placed in the presence of enzyme of amyloglucosidase type (e.g.: Optimax 7525 HP, Optidex L300 from the company GENENCOR International, Box 642, 2600 AP Delft, Netherlands, Amg 300 L from the company Novo Nordisk Bioindustries S.A., 79, av Francois-Arago, 92017 Nanterre Cedex, France, G-990 or Ambazyme LE300 from RHODIA, Poleacre Lane, Woodley, Stockport, Cheshire, SK6 1 PQ, United Kingdom) and viscosity-reducing enzyme (e.g.: Econase CE from the company Alko Biotechnology, SF-05200 Rajamaki, Finland, Celluclast from the company Novo Nordisk Bioindustries S.A., 79, av. Francois-Arago, 92017 Nanterre Cedex, France; β-Glucanase 750 L from RHODIA, Poleacre Lane, Woodley, Stockport, Cheshire, SK6 1PQ, United Kingdom).

Depending on the saccharification enzymes used, the pH must be adjusted with approximately 96% sulphuric acid or any other acidifying agent. The flow rate of acid is controlled using a pH probe installed at the saccharification inlet. The pH may range between 3 and 7 depending on the optimum characteristics of the enzymes used.

Enzymes with protease activity (such as Proteinase 200 L from RHODIA, Poleacre Lane, Woodley, Stockport, Cheshire, SK6 1PQ, United Kingdom) and/or pullulanase (such as Ambazyme P20 from RHODIA, Poleacre Lane, Woodley, Stockport, Cheshire, SK6 1PQ, United Kingdom or Optimax L300 from GENENCOR, P.O. Box 642, Delft, Netherlands) may also be used depending on the types of substrates, in order, respectively, to degrade the proteins present in the liquefied must which is a potential source of nitrogen for the fermentation organisms, or to complete the enzymatic hydrolysis of the starch (pullulanases have a specific action on the α1–6 linkage).

The flow rates of the enzymes may be controlled by the flow rate of flour entering and also depend on the laboratory analyses relating to the concentration of glucose produced and the remaining starch content; the object of this operation is to arrive at the end of saccharification or of fermentation (depending on the processes adopted) with an absence of starch remaining in the wine entering the distillery. These flow rates are thus controlled as a function of the enzymatic activity specific to each type of enzyme.

The current enzyme-dependent characteristics used for the saccharification process are:

Temperature: 55–65° C.

pH: 4 to 4.5

Solids content: 28%–35%

Residence time: 15–20 hours (Example 1A): or between 8–13 hours (Example 1B)

Flow rate of saccharification enzyme: about 4.5 litres/hour for a flour feed rate of 8 tonnes/hour Flow rate of viscosity-reducing enzyme: about 1.5 litres/hour for a flour feed rate of 8 tonnes/hour.

The saccharification uses five 90 m$^3$ tanks (function of Examples 1A and 1B).

The 5 saccharification tanks have mechanical stirring (stirrers of SEW-USOCOME or PMS brand, BP 72 91560 Crosne, stirring speed 24 rpm), this stirring allowing good homogenization of the must during saccharification and consequently a facilitated contact between the enzymes and the starch to be hydrolysed.

The saccharified must is cooled to 32° C. (temperature between 30 and 34° C., so as not to inhibit the growth and fermentation of the yeasts used) in conventional heat exchangers before being conveyed to the next plant.

Two embodiments of the process may be carried out. They consist in carrying out the total or partial bioconversion of macromolecular starch into fermentable glucose molecules. In the second case (very partial hydrolysis), the saccharification takes place during the fermentation step, the residence time in the saccharification being much shorter than in the first case (virtually total hydrolysis).

Prefermentation

The prefermentation or propagation of the yeasts (e.g.: *Saccharomyces cerevisiae, Saccharomyces pombe*, etc.) may be advantageously carried out to obtain a concentration at least equal to 10$^7$ cells per milliliter in 4 prefermenters (volume of the prefermenters: 45 m$^3$ each) operating in parallel.

The saccharified must derived from the saccharification is diluted with water or vinasse to obtain a weak must (water flow rate: 7 to 8 m$^3$/h for a saccharified must flow rate of 4–5 m$^3$/h, so as to obtain a glucose concentration in the weak must ranging between 50 and 90 g/l) which is distributed among the 4 prefermenters and serves as growth substrate for the microorganisms. The water may be a borehole water, a process liquor (evaporation condensates, aqueous distillates or water derived from the starch refinery) or a river water prefiltered through a sand bed and/or sterilized by UV radiation.

The temperature in the prefermenters is rigorously monitored and controlled by a system of cooling plates in which a cooling liquid circulates inside or outside the prefermentation tanks.

Any multiplication of microorganisms results in a temperature increase. Any variation in temperature may become inhibitory on the propagation of the yeasts.

The temperature in the prefermenters is maintained at between 30 and 35° C.

In order to promote the growth of the yeasts, the nutrient medium required for these microorganisms to multiply comprises nitrogen supplied in various forms such as urea, ammonia or ammonium salts, phosphorus supplied in various forms such as phosphoric acid or phosphates, sulphur supplied in various forms such as sulphuric acid or sulphates, oxygen, fermentable sugars, essential minerals if any deficiency is detected.

These nutrient elements prevent any slowing down of the propagation of the yeasts.

These nutrient elements and oxygen in the form of compressed air (or aqueous hydrogen peroxide solution) are supplied steadily in order to promote the growth of the yeasts rather than alcoholic fermentation.

By way of example:

the air flow rate in each prefermenter is about 30 Nm$^3$/h;

5 kg of ammonium sulphate with a minimum nitrogen content of 21% and a maximum water content of 0.2% (HOLVOET Chimie Chaussee de Leuze 144, Leuzesesteenweg Belgium; INTERFERT, 28 rue d'Armenonville, 92200 Neuilly sur Seine, etc.) and 5 kg of diammonium phosphate with a minimum purity of 95% and a P$_2$O$_5$ content of between 52 and 55% (RHODIA Chimie, 299, rue du Président Pompidou, BP 202, 59561 La Madeleine Cedex; PRAYON France, 80–82 rue de Paris, 93804 Epinay sur Seine Cedex) are added every hour to each prefermenter in the form of an aqueous solution.

In order to avoid any risk of infection with foreign microorganisms, since the industrial plant is open to the air, the prefermenters are cleaned and disinfected in turn by cleaning with filtered river water and then by injecting steam for a minimum preset period of 10 minutes.

This moreover makes it possible to avoid infections with "wild-type" yeasts and gradual degeneration of the predominant yeast strain.

An identification of these contaminant microorganisms detected on the site was performed: this microorganism is Brettanomyces bruxellensis.

This contaminant yeast has a characteristic elongate shape which is very different from the morphology of the *Saccharomyces cerevisiae* used.

Daily observations by microscope (universal transmission light microscope of the ZEISS brand, magnification×400) of the yeasted musts were set up at the manufacturing site to allow an instantaneous detection of the appearance of these wild-type yeasts of Brettanomyces type.

Counting and morphological recognition operations on Petri dishes give a posteriori confirmation of the observations by microscope.

The medium used for the counting on Petri dishes, known as MALT WICKERHAM medium, is made up, for 2 litres of preparation, of:

3 g malt extract (reference: Laboratoire Merck 105391)
5 g peptone (reference: Laboratoire Merck 7212)
3 g yeast extract (reference: Laboratoire Merck 103753)
10 g glucose
10 g nutrient agar (reference: Laboratoire Merck 1614)

The sample of the yeasted must is subjected to serial tenfold dilution in physiological saline (9 per thousand NaCl solution) until the following dilutions are obtained: $10^{-5}$; $10^{-6}$; $10^{-7}$. 1 ml of these dilutions is deep-inoculated according to the conventional techniques of microbiology with the MALT WICKERHAM medium.

The gap in the frequency of addition of the desired strain for the fermentation process consequently leads to a predominant contamination with the undesirable microorganism, resulting in an increase in the fermentation times and an impairment in the quality of the spirituous liquors produced (e.g.: increase in the ester content).

This phenomenon was observed irrespective of the variants of the present process.

A delay in the imperative frequency of addition of the desired strain and in replacement of the old yeasts moreover results in the need to accelerate the additions of yeasts in order to eradicate the persistence of the contamination due to the recycling of the clear vinasse, containing contaminant organisms, into the slurrying operation.

Process for Replacing the Old Yeasts with Fresh Yeasts

During the propagation of fresh yeasts, for example one prefermenter in four is chosen to carry out this operation, and the actions to be performed are as follows:

With the prefermenter emptied, wash it with water and then steam-clean it (for example: pressure =3 bar absolute, temperature =130° C.) for a minimum preset time of 10 minutes.

This cleaning can also be carried out with aqueous formaldehyde (30.5% formaldehyde: Caldic France B.P. 722 51056 REIMS) or any conventional disinfectant, such as:

the family of halogen compounds: chlorine or iodine and derivatives thereof;

oxidizing agents (hydrogen peroxide, potassium permanganate);

amine compounds (Bactanios 95 used as a 0.2 to 0.5% solution, Anios Pav é du Moulin 59260 Lille Hellemmes);

strong acids and bases (concentrated 96% sulphuric acid used at a dilution of 5 to 10%, Tessenderlo Chemie, rue du Trône 130 B Brussels), (concentrated 30.5% caustic soda, used while hot at a dilution of 1 to 2%, CLEMENT RPC Ets LOMME, rue Pelouze, BP 117 59461 LOMME cedex), (Agrobac used at dilutions of 2 to 7.5%: MINOT APURA, 88 rue de Marquillies 59044 LILLE cedex), (Agromousse used at dilutions of 5 to 7%, MINOT APURA, 88 rue de Marquillies 59044 LILLE cedex), (Aniosteril disinfectant acid used at doses of 1 to 1.5%, Anios Pavé du Moulin 59260 Lille Hellemmes), (GALOR C7 used at doses of 1 to 5%, Anios Pavé du Moulin 59260 Lille Hellemmes);

aldehydes and surfactants (Anios W4 used at 0.5% as a spray, contact time: 5 to 10 minutes, or in circulation at 0.4%, contact time: 20 to 30 minutes, Anios Pavé du Moulin 59260 Lille Hellemmes).

The percentages indicated above are expressed on a weight basis.

The cleaning-disinfecting procedure may comprise 5 stages:

prewashing or precleaning: mechanical removal of the coarse soiling with a jet of water, cleaning: removal of the rest of the soiling with a cleaning solution, rinsing: removal of the cleaning solution in which the soiling is dispersed, disinfecting: chemical destruction of the surface biocontamination using a disinfectant solution, final rinsing: removal of the residual disinfectant solution.

A combination of the operations mentioned above makes it possible in all cases to achieve a sufficient disinfection of the prefermenter intended to receive the fresh yeasts without contamination with the old yeasts.

The prefermenter is filled to about one third of its volume with weak must which is slightly more dilute than normal.

The temperature in the prefermenter is rigorously controlled (below 34° C.).

The 300 kg of fresh yeasts with a solids content of about 32% are added to the prefermenter.

A supply of nutrient salts and air is provided and controlled.

Feeding with weak must is continued while at the same time monitoring the density and the temperature in the prefermenter.

Once filled, the prefermenter is placed in communication successively with the other prefermenters which have been emptied, cleaned and sterilized with steam or chemically beforehand so as not to contaminate the fresh yeasts with the old ones.

The 4 prefermenters are thus gradually fed with the fresh yeasts.

Fermentation

The alcoholic fermentation may be carried out using saccharified must obtained from the saccharification, at a flow rate of 14 to 22 m³/h until the sugar content of the wine obtained is less than 3 g/l, preferably less than 2 g/l and better still less than 1 g/l, for an alcoholic degree of the wine of at least 9.5% by volume.

Two types of fermentation may be performed:

"batch" or discontinuous fermentation, in which process each fermenter operates individually, i.e. the fermentation is carried out to completion in each fermenter;

continuous fermentation, in which process the fermenters work in cascade, i.e. the fermentation is only partial in each fermenter until the last one, in which the fermentation is completed.

"Batch" or Discontinuous Fermentation

Each fermenter is inoculated alternately with the yeasted must obtained from the prefermenters.

The prefermented must is conveyed according to the following process:

1 prefermenter (volume: 45 m$^3$) is completely emptied into the fermenter;

the other 3 are partially transferred in parallel to make up the "yeast stock" in the fermenters.

The total volume of yeasted must transferred corresponds to about 30–70% of the volume of the fermenter. the temperature in the fermenters is maintained at between 0 and 35° C.

The fermentation uses two 90 m$^3$ tanks and six 180 m$^3$ tanks. The fermented must is then transferred into wine vats before being fed into the distillery plant.

Continuous Fermentation

The fermenters are no longer fed alternately with yeasted must and saccharified must as described above, but rather according to the following process:

Yeasted must and saccharified must are fed continuously to the fermenter or the first two or three fermenters, referred to as the head fermenters, the following fermenters being referred to as the fall-off fermenters.

The feed rates into the head fermenters may be as follows:

Yeasted must: 9 to 16 m$^3$/h

Saccharified must: 15 to 25 m$^3$/h

The temperature in the fermenters is kept at between 30 and 35° C.

Cascade fermentation then continues in each fermenter until the sugar content of the wine obtained is less than 3 g/l, preferably less than 2 g/l and better still less than 1 g/l, for an alcoholic degree of the wine of at least 9.5% by volume, and the fermented must in the last fermenter is then conveyed, continuously still, to the wine vats, before being fed into the distillery plant.

In this type of continuous fermentation, the fermentation time is calculated by dividing the filling volume of musts fermenting in all of the fermenters by the wine feed rate of the distillery columns. The same fermentation times are obtained in continuous fermentation as in batch fermentation.

The alcoholic degree of the wines is determined enzymatically using the YSI 2700 SELECT biochemical analyser (ROUCAIRE, 2 av. du Pacifique BP 78 Les Ulis 91493 Courtaboeuf cedex). The sample of wine is diluted 50-fold with demineralized water. This sample is filtered and is then fed into the YSI 2700 SELECT biochemical analyser which automatically gives the ethanol content in g/l. In order to obtain the result in alcoholic degrees (volume-for-volume percentage), it suffices to divide this value by 7.88, after the dilution factor has been taken into account.

The remaining glucose content is determined enzymatically using the YSI 2300 STAT PLUS biochemical analyser (ROUCAIRE, 2 av. du Pacifique BP 78 Les Ulis 91493 Courtaboeuf cedex). The necessary dilutions of the samples are carried out according to the assumed remaining glucose content. The sample is filtered and is then fed into the YSI 2300 STAT PLUS biochemical analyser, which gives a remaining glucose content expressed in mg/dl. In order to obtain it in g/l, it suffices to multiply the result obtained by 100, after the possible dilution factor has been taken into account.

Production of Spirituous Liquors (Crude Alcohol)

The distillation column(s) (suppliers: KREBS-SPEICHIM, 14 rue Hoche, 92800 PUTEAUX, JAAKKO-P ÖYRY, Garden Part-Dieu, 65 Bd Vivier Merle 69482 LYONS CEDEX 03), which can operate in parallel or in series (twofold effect) under vacuum or under pressure, are heated with the vapours derived, for example, from the concentration of vinasse (distillery co-products) in order to improve the thermal efficiencies of the unit, by direct injection, by means of stills or by thermal compression. These vapours also heat the Lutter columns.

The fermented must or wine obtained from the fermentation, after passage through a heat exchanger, feeds in parallel the distillation columns. The alcohol vapours from the columns are condensed in heat exchangers.

The vinasse leaving at the bottom of the columns is conveyed to the spent-grain separation plant to be clarified (separation of the soluble matter from the insoluble matter) before being conveyed to the vinasse concentration plant.

The alcohol or spirituous liquor is concentrated to 90–96% by volume (depending on the investment constraints) in the distillation column(s) and then cooled in exchangers before storage. An extraction of the volatile impurities is also carried out on the distillation column(s) in order to improve the quality of the spirituous liquors (according to the desired ester content). These unpleasant tastes extracted which are more difficult to upgrade are stored in a separate tank.

The examples which follow illustrate the invention.

EXAMPLE 1A

Saccharification Time =15–20 hours (Test with Wheat)

All the saccharification tanks are filled, in order to obtain a virtually total enzymatic hydrolysis of the starch molecules into fermentable sugars. The plant throughput is about 24 m$^3$/h of saccharified must.

The old yeasts are replaced at a frequency of less than 4 days with 300 kg of yeasts (e.g.: *Saccharomyces cerevisiae*) pressed to a solids content of 32%; each gram of product contains about 10×10$^9$ live cells, for a weak must with a glucose concentration of 50–90 g/l depending on the plant throughput (flow rate of weak must: 12–13 m$^3$/h). The use of freeze-dried yeasts or commercial concentrated creams of yeasts (*Saccharomyces cerevisiae* or *pombe*) also gives the same result (yeast suppliers: LALLEMAND S.A., Complexe scientifique Rangeuil, Hall Gilbert Durand 3, BP 412 , 31405 Toulouse Cedex 4; LESAFFRE, 41, rue Etienne Marcin, 75001 Paris, etc.).

A fermentation time of 18 to 24 hours (average: 20 hours) with an alcoholic degree of the wine obtained of greater than 9.5% minimum by volume and a remaining sugar concentration of less than 1 g/l were thus observed, as opposed to 35 to 45 hours with remaining sugar concentrations which may be suddenly and sporadically up to 20–30 g/l under the industrial conditions generally employed (the conventional fermentation times on starchy substrate recommended by the manufacturers or given in the literature are about 40 to 60 hours).

The fermentation time is calculated as follows: the time for filling the fermenter with saccharified must is added to the fall-off time (i.e. the time taken to obtain a residual glucose content in the region of 0 g/l, i.e. the time taken to convey the wine for distillation, if a residual glucose content in the region of 0 g/l cannot be obtained).

An ester content in the crude alcohol (spirituous liquors) produced after simple distillation of less than 300 ppm without extraction of volatile impurities (i.e. a more than 50% reduction compared with the ester content generally obtained) was also obtained.

EXAMPLE 1B

Saccharification Time =About 8–13 hours (Test with Wheat)

Some saccharification tanks are bypassed, in order to obtain a very partial enzymatic hydrolysis of the starch molecules into fermentable sugars. The plant throughput is about 24 m$^3$/h of saccharified must.

The old yeasts are replaced at the same frequency and to the same amount with yeasts (e.g.: *Saccharomyces cerevisiae*) pressed to a solids content of 32%.

A fermentation time of 22 to 30 hours (average: 25 hours) with an alcoholic degree of the wine obtained of greater than 9.5% minimum by volume and a remaining sugar concentration again less than 1 g/l were thus observed, as opposed to 35 to 45 hours with remaining sugar concentrations which may be suddenly and sporadically up to 20–30 g/l under the industrial conditions generally employed (the conventional fermentation times on a starchy substrate which are recommended by the manufacturers or given in the literature are about 40 to 60 hours).

An ester content in the crude alcohol (spirituous liquors) produced after simple distillation of less than 300 ppm without extraction of volatile impurities (i.e. a more than 50% reduction compared with the ester content generally obtained) was similarly obtained.

EXAMPLE 2A

Test with Corn

Corn (starch =61–78%, proteins =6–12%), used as starchy substrate, was subjected to the industrial process as described in Example 1A. The plant throughput is about 20–24 m$^3$/h of saccharified must.

The yeasts (e.g.: *Saccharomyces cerevisiae*), pressed to a solids content of 32%, are replaced at the same frequency and to the same amount.

A fermentation time of 18 to 24 hours with an alcoholic degree of the wine obtained of greater than 9.5% minimum by volume and a remaining sugar concentration again less than 1 g/l were thus observed.

An ester content in the crude alcohol (spirituous liquors) produced after simple distillation of less than 300 ppm without extraction of volatile impurities (i.e. a more than 50% reduction compared with the ester content generally obtained) was similarly obtained.

EXAMPLE 2B

Test with Barley

Barley (starch =65–75%, proteins 8–15%), used as starchy substrate, was subjected to the industrial process as described in Example 1A. The plant throughput is about 20–24 m$^3$/h of saccharified must.

The yeasts (e.g.: *Saccharomyces cerevisiae*), pressed to a solids content of 32%, are replaced at the same frequency and to the same amount.

A fermentation time of 18 to 24 hours with an alcoholic degree of the wine obtained of greater than 9.5% minimum by volume and a remaining sugar concentration again less than 1 g/l were thus observed.

An ester content in the crude alcohol (spirituous liquors) produced after simple distillation of less than 300 ppm without extraction of volatile impurities (i.e. a more than 50% reduction relative to the ester content generally obtained) were similarly obtained.

Comparative Example

Test of Partial Re-inoculation with Fresh Yeasts

Tests of partial re-inoculation of the prefermenters with fresh *Saccharomyces cerevisiae* yeasts are carried out.

All the saccharification tanks are filled, in order to obtain as complete as possible an enzymatic hydrolysis of the starch molecules into fermentable sugars (similar to Example 1A). The plant throughput is about 24 m$^3$/h of saccharified must.

200 kg of yeasts (*Saccharomyces cerevisiae*), pressed to a solids content of 32%, are supplied at a frequency again of less than 4 days, for a weak must with a glucose concentration of 50–90 g/l depending on the plant throughput (flow rate of weak must =12–13 m$^3$/h).

The yeasts are no longer added, as in Example 1A, into a prefermenter which has been washed and cleaned beforehand, but instead the 200 kg are distributed evenly among the 4 prefermenters (50 kg in each prefermenter) in which old contaminated yeasts remain (about 25 m$^3$ of must in each prefermenter).

The results described in Example 1A above are not obtained and no improvement is observed either in the fermentation times or in the quality of the spirituous liquors distilled: the fermentation times remain at about 35 to 45 hours with remaining sugar concentrations which may be suddenly and sporadically up to 20–30 g/l, and the ester content is greater than 300 ppm without extraction of volatile impurities.

What is claimed is:

1. A process for producing ethanol comprising:
    placing a starchy plant raw material must in contact with a liquefaction enzyme in order to obtain a liquefied must;
    placing the liquefied must in contact with a saccharification enzyme in order to obtain an at least partially saccharified must;
    preparing in a prefermenter a suspension of yeasts of the genus Saccharomyces in a nutrient medium;
    placing the saccharified must in contact with an amount of the yeast suspension which is sufficient and for a time which is sufficient to convert the sugars contained in the saccharified must into ethanol, giving a wine with a sugar content of less than 3 g/l for an alcoholic degree of at least 9.5% on a volume-for-volume basis; and
    distilling the wine in order to obtain ethanol,
    wherein said yeast suspension in the prefermenter is maintained by removing substantially all the yeasts present in the prefermenter, cleaning and disinfecting the prefermenter, and replacing the yeasts therein with fresh yeasts at a time interval such that the concentration of microorganisms, other than the yeasts of the genus Saccharomyces, in the prefermenter remains less than a given threshold during the interval following the replacement of the yeasts.

2. The process according to claim 1, wherein said threshold is less than 10$^7$ cells per milliliter.

3. The process according to claim 1, wherein said threshold is less than $10^6$ cells per milliliter.

4. The process according to claim 1, further comprising replacing all the yeasts in the prefermenter with fresh yeasts as soon as a microorganism of elongate shape is observed by microscope.

5. The process according to claim 1, further comprising replacing all the yeasts in the prefermenter with fresh yeasts at a time interval of less than 4 days.

6. The process according to claim 1, further comprising replacing all the yeasts in the prefermenter with fresh yeasts in an amount such that a concentration at least equal to $10^6$ cells per milliliter is obtained in the prefermenter.

7. The process according to claim 1, further comprising diluting a first portion of 10 to 30% of the weight of the saccharified must in order to obtain a weak must, the rest of the saccharified must constituting a strong must, in prefermenting the weak must in the prefermenter to obtain a prefermented must and in placing the strong must in the presence of the prefermented must in a fermenter for a time which is sufficient to obtain the wine.

8. The process according to claim 1, comprising placing the saccharified must in contact with the yeast suspension at a temperature of 30 to 35° C.

9. The process according to claim 1, wherein said plant material is wheat.

10. The process according to claim 1, wherein said plant material is corn, barley, rice, rye, or sorghum.

11. A process according to claim 1 wherein said wine has a sugar content less than 2 g/l for an alcoholic degree of at least 9.5% on a volume-for-volume basis.

12. A process according to claim 1 wherein said wine has a sugar content less than 1 g/l for an alcoholic degree of at least 9.5% on a volume-for-volume basis.

13. The process according to claim 1, comprising replacing all the yeasts in the prefermenter with fresh yeasts in an amount such that a concentration at least equal to $10^7$ cells per milliliter is obtained in the prefermenter.

14. The process according to claim 1, comprising diluting a first portion of 15 to 20% of the weight of the saccharified must in order to obtain a weak must, the rest of the saccharified must constituting a strong must, in prefermenting the weak must in the prefermenter to obtain a prefermented must and in placing the strong must in the presence of the prefermented must in a fermenter for a time which is sufficient to obtain the wine.

* * * * *